United States Patent [19]

Preziosi et al.

[11] Patent Number: 4,735,745

[45] Date of Patent: Apr. 5, 1988

[54] DEFROST INDICATOR

[75] Inventors: Anthony F. Preziosi, Ledgewood; Thaddeus Prusik, Roosevelt; Ray H. Baughman, Morris Plains, all of N.J.

[73] Assignee: LifeLines Technology, Inc., Morris Plains, N.J.

[21] Appl. No.: 373,955

[22] Filed: May 3, 1982

[51] Int. Cl.$^4$ .................. G01N 31/00; G01D 21/00
[52] U.S. Cl. ................... 252/408.1; 428/913; 252/962; 116/207; 116/216; 374/161; 374/162; 374/141
[58] Field of Search ............ 526/285; 252/600, 408.1, 252/962; 116/207, 216, 217, 219; 374/161, 162, 141; 106/DIG. 6; 428/913

[56] References Cited

U.S. PATENT DOCUMENTS

| | | | |
|---|---|---|---|
| 3,501,297 | 3/1970 | Cremeans | 250/474.1 |
| 3,615,719 | 10/1971 | Michel et al. | 62/130 |
| 3,994,867 | 11/1976 | Baughman | 526/285 X |
| 3,999,946 | 12/1976 | Patel et al. | 252/962 |
| 4,195,055 | 3/1980 | Patel | 422/58 |
| 4,195,056 | 3/1980 | Patel | 422/58 |
| 4,195,057 | 3/1980 | Patel | 422/58 |
| 4,195,058 | 3/1980 | Patel | 422/58 |
| 4,215,208 | 7/1980 | Yee et al. | 116/202 |
| 4,220,747 | 9/1980 | Preziosi | 526/285 |
| 4,228,126 | 10/1980 | Patel | 436/2 X |
| 4,298,348 | 11/1981 | Ivory | 436/7 |
| 4,339,240 | 7/1982 | Patel | 422/56 X |
| 4,356,256 | 10/1982 | O'Brien et al. | 430/495 X |
| 4,373,032 | 2/1983 | Preziosi et al. | 526/285 X |
| 4,389,217 | 6/1983 | Baughman | 422/56 X |
| 4,439,346 | 3/1984 | Patel et al. | 252/408.1 |

Primary Examiner—Richard D. Lovering
Assistant Examiner—Catherine S. Kilby
Attorney, Agent, or Firm—Arthur J. Plantamura

[57] ABSTRACT

A new process is described which is useful for producing novel articles of manufacture useful for monitoring the time-temperature history of perishable items. The process initially involves forming a solution comprised of a diacetylenic monomer and a solvent. The solution is frozen, and the frozen solution having crystalline diacetylenic monomer therein is irradiated to partially polymerize the diacetylenic monomer. Partial polymerization of the crystalline diacetylenic monomer admixed with frozen solvent results in the production of a novel article of manufacture having color. The novel article of manufacture is comprised of frozen solvent, diacetylenic monomer, and colored polydiacetylene. Due to the intensity of the color of the polydiacetylene, the entire article of manufacture appears to be colored.

The colored article of manufacture may be attached to various perishables to monitor the shelf life of the perishables. Upon exposure to temperatures above a critical temperature, the frozen solvent melts and extracts unreacted monomer from the colored polymer, thereby causing a sharp color transition which indicates that the perishable should possibly be discarded.

11 Claims, 1 Drawing Sheet

DEFROST INDICATOR

BACKGROUND OF THE INVENTION

This invention relates to a process in which various diacetylenic compounds are utilized to indicate via irreversible color transformations whether perishable commodities such as frozen foodstuffs, pharmaceuticals, vaccines etc. have been exposed to temperatures above a critical temperature which result in substantial degradation of such products.

U.S. Pat. No. 4,215,208 (Yee et al., 1980) discloses that certain diacetylenic compounds may be polymerized via radiation, and that the resulting polymers are capable of undergoing reversible color changes with changing temperatures. In regard to the above-referenced patent, Yee et al. describes a TEMPERATURE-INDICATOR DEVICE UTILIZING THERMOCHROMIC POLYACETYLENES which functioned most effectively in the temperature region of 120°–200° C.

U.S. application Ser. No. 938,292, filed Aug. 30, 1978, by G. N. Patel and D. M. Ivory, now U.S. Pat. No. 4,439,346 (Mar. 27, 1984) (see also U.S. Pat. No. 4,452,995 issued June 5, 1984 on a division thereof) discloses that mixtures of polydiacetylenes and gel forming liquids may be utilized to construct a clinical thermometer which undergoes a color transformation when a predetermined temperature has been reached. The composition reverts to the original color upon cooling to a temperature substantially below the original temperature color transformation point. The process described by Patel and Ivory involves polymerizing a diacetylenic monomer via radiation, extracting any unreacted monomer from the polymerized material with an organic solvent, and finally obtaining the color transformation by heating the polymeric gel solution to the desired temperature which is a function of the particular components of the polymeric gel solution.

U.S. Pat. No. 4,195,055 (Patel, 1980) describes a device which measures the time-temperature exposure of perishable articles. The device utilizes a process wherein solutions of various color responsive materials (dyes, pigments, partially polymerized diacetylenes etc.) are deposited upon a substrate followed by subsequent evaporation of the solvent, and then contacting the substrate with a vapor. Upon contact with said vapor, the color responsive material undergoes a color change and simultaneously creates a moving boundary which advances along a diffusion strip as a function of time and temperature. Various modifications of the device are described in the following patent assigned to Allied Chemical Corporation: U.S. Pat. Nos. 4,195,056 (1980); 4,195,057 (1980); 4,195,058 (1980).

U.S. Pat. No. 3,615,719 (Michel et al., 1971) describes a process for determining whether frozen foods have been exposed to cumulative time-temperature exposures which result in spoilage of frozen products. The above-referenced process involves freezing an indicating liquid which is separated from a color indicating substrate (absorbent material such as blotting paper) by an intermediate layer composed of egg white, albumin, glue, gelatin, or molten sugar of a glassy consistency. Upon thawing, the indicating liquid begins to dissolve the intermediate layer, and when said intermediate layer is completely dissolved the thawed liquid interacts with the substrate causing color development of the substrate or a color change in the substrate. The liquid indicators used in the process are self-dyeing staining reagents or colorless solutions with dissolved reagents which react with reagents on the substrate to develop color or to effect the color transformation of the substrate.

BRIEF DESCRIPTION OF THE INVENTION

The present invention relates to a novel process which comprises the steps:

(a) dissolving a diacetylenic monomer in a solvent to form a solution of monomer and solvent;

(b) freezing said solution to crystallize the diacetylenic monomer to form an intimate mixture of a phase of crystallized monomer and a solid solvent phase;

(c) irradiating said phase of crystallized monomer to partially polymerize said crystallized monomer to form a phase of unpolymerized colorless monomer and colored polydiacetylene;

wherein said monomer is soluble in said solvent above the freezing point of said solvent.

The present invention also includes a novel article of manufacture which comprises frozen crystalline diacetylenic monomer admixed with a solid solvent phase as represented by FIG. 2. The invention includes an additional novel article of manufacture which comprises a phase of unpolymerized diacetylenic monomer and colored polymer admixed with the solid solvent phase as represented by FIG. 3. In each article of manufacture, said monomer is soluble or partially soluble in said solvent above the melting point of said solid solvent phase. Additionally, the invention includes perishable products having attached thereto the articles of manufacture of the present invention.

The above described invention is advantageous in that the articles of manufacture derived from the novel process may be used as defrost indicators for perishable commodities. More specifically, the article of manufacture which comprises crystalline diacetylenic monomer dispersed in a solid solvent phase may be affixed to various perishable commodities. Irradiation is utilized to effect partial polymerization of the diacetylenic monomer which results in the development of color 1 (e.g., blue) in the partially polymerized material and in the production of the additional article of manufacture previously described. Upon exposure to undesirable temperatures, the solid solvent phase melts and extracts the unreacted monomer from the colored partially polymerized diacetylene, said extraction being accompanied by a color transition from color 1 to color 2 (e.g. blue to red) thereby indicating that the perishable has had an excessive exposure to temperatures above a critical temperature which is chosen because it may cause degradation of the perishable.

DETAILED DESCRIPTION OF THE INVENTION

In accordance with this invention, there is provided a novel process for producing novel articles of manufacture. The novel articles of manufacture can be utilized to indicate whether various perishables such as foodstuffs, vaccines, blood and the like, have been exposed to undesirable temperatures which may result in the degradation of the perishable article.

The novel articles of manufacture of the present invention are referred to as defrost indicators. The defrost indicators can be constructed from diacetylenic monomer compounds which polymerize in the solid state when exposed to high energy radiation such as ultraviolet light, x-rays or gamma rays. The term diacetylenic monomer is defined as an acetylenic compound containing at least two conjugated acetylene groups.

By the term "solid state" is meant a physical state which can be completely amorphous, substantially crystalline, or amorphous with crystalline regions randomly located within the solid. It is preferred to use substantially crystalline monomers for producing the defrost indicators, since the desired polymerizability is enhanced by using monomers which are substantially crystalline.

The term polydiacetylenes is used herein to describe polymers produced by 1,4-addition of the diacetylenic monomers which are used in the practice of this invention.

The diacetylenic monomers for producing the the defrost indicators are generally colorless and undergo a color change when exposed to radiation. However, the choice of chromatic substituent groups R on the diacetylenic monomer can result in a colored initial state. Likewise, it is sometimes desirable to use commingled dyes, pigments or diacetylenes to enhance color changes. The color changes which are associated with the radiation responses of the indicators correspond to intermolecular 1,4-addition polymerization reactions between adjacent $C\equiv C-C\equiv C$ functionalities. These addition reactions result in the production of polydiacetylenes. Polydiacetylenes have a highly conjugated backbone. The color of the polymer chain is due to this unsaturated backbone.

Figure 1:
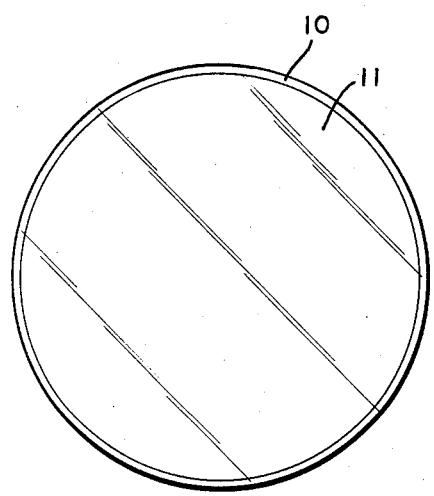
FIG. 1 is a view of a colorless solution 11 in a closed container 10 as used in the present invention.
Figure 2:
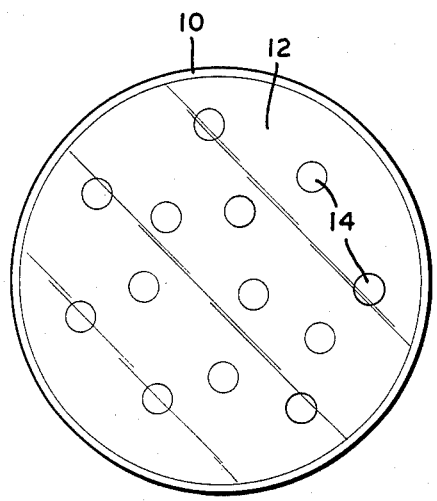
FIG. 2 is a cross section microscopic view of an article of manufacture as used in the present invention showing a phase of crystallized monomer 14 dispersed in a solid solvent phase 12.
Figure 3:
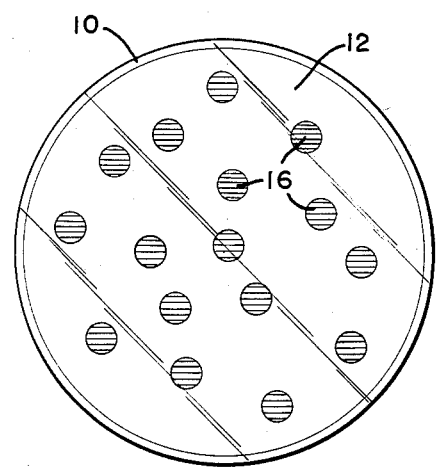
FIG. 3 is a cross section microscopic view of an article of manufacture as used in the present invention showing a phase 16 of unpolymerized colorless monomer and colored polydiacetylene dispersed in a solid solvent phase 12.

In general, in order to construct the defrost indicators which are the subject of this invention, a diacetylenic monomer is initially dissolved in an appropriate solvent (FIG. 1). The monomers are essentially inactive while in solution. Subsequent to forming the monomer solvent solution, the solution is frozen thereby forming a novel article of manufacture as represented by FIG. 2. The novel article of manufacture comprises a phase of crystalline diacetylenic monomer 14 dispersed in a solid solvent phase 12. The described article of manufacture is generally colorless and is also essentially inactive. Activation of the article of manufacture is the next step and is accomplished via high energy irradiation. Activation of the phase of diacetylenic monomer 14 which is dispersed in the solid solvent phase 12 results in the typically colorless article of manufacture changing to a first color, in most cases blue. The blue color is the result of partial polymerization of the monomer. The above described activation or partial polymerization results in the production of an additional novel article of manufacture as represented by FIG. 3. It will be appreciated that FIG. 3 is a microscopic view of the novel article of manufacture, and that a macroscopic view of the article results in a completely blue image. It will further be appreciated that blue is the predominant color for the practice of this aspect of the invention, but that other colors are also possible. This novel article of manufacture comprises a phase 16 consisting essentially of unpolymerized generally colorless monomer and colored polymer which is dispersed in the solid solvent phase 12. The activated article of manufacture can be attached to various perishable articles.

Figure 4:
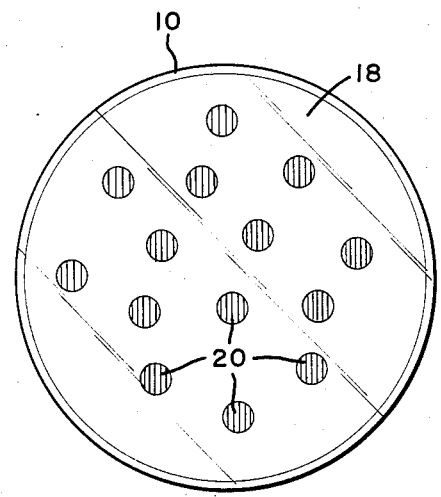
FIG. 4 is a microscopic view of an indicator exposed to temperatures above a critical temperature derived from the use of the articles of manufacture and process of the present invention showing thawed solvent 18 with dissolved monomer and colored polymer 20.

It is instructive to note that activation of the article of manufacture may be effected subsequent to the attachment of the article to the perishable. Whether activation of the article of manufacture is effected prior to or subsequent to attachment is a matter for the particular user to determine based on his specific requirements. When the subject perishable with an attached activated defrost indicator is exposed to undesirable temperatures in regard to the particular perishable, the solid solvent phase melts and extracts the unpolymerized monomer from the polymer. The extraction results in an irreversible color transformation as represented by FIG. 4 (e.g. blue to red) with colored polymer 20 being dispersed in thawed solvent 18 containing dissolved monomer, thereby indicating that the perishable article has been exposed to temperatures which may cause degradation of the product, and therefore the product should possibly be discarded. Again, it will be appreciated that red is the predominant color for the practice of this aspect of the present invention, and that colors other than red are possible.

The term solid solvent phase is defined as a continuous phase that forms upon freezing principally solvent. In cases where the monomer is relatively insoluble in the solid solvent near the melting point of the solvent, the solid solvent phase will normally contain essentially only solvent. In cases where the monomer is more soluble in the solid solvent near the melting point of the solvent the solid solvent phase will contain an appreciable amount of monomer. Additionally, if the solution contains significant amounts of third components such as co-solvents and or melting point depressants, then these components may also be found in the solid solvent phase.

The term melting point of solid solvent phase is defined as the temperature at which a significant amount of solid solvent phase melts. If the solid solvent phase contains essentially only solvent then this temperature will approximate the melting point of the pure solvent. If on the other hand, significant amounts of monomer and or other third components are present in the solid solvent phase, then the melting point of the solid solvent phase will be somewhat less than the melting point of the pure solvent.

By the term "a phase of crystallized monomer" is meant a solid phase containing principally diacetylenic monomer as defined above.

The term "a phase of unpolymerized colorless monomer and colored polydiacetylene" is defined as a solid phase that results from the partial polymerization of the phase of crystallized monomer.

The diacetylenic compounds most useful in the practice of this invention are of the general formula $R_1-C\equiv C-C\equiv C-R_2$ wherein $R_1$ and $R_2$ are the same or different. Examples of $R_1$ and $R_2$ groups in the above formula may be alkyl, alkoxyalkyl, aryl, benzoates, sulfonates, urethanes, alcohols, acids, and the like.

In many preferred embodiments of this invention diacetylenic compounds containing urethane groups (i.e. "diurethane diynes") are used to construct the defrost indicators. The described diacetylenic urethane compounds are represented by the formula R"NHOCO—$(CH_2)_n$—C≡C—C≡C—$(CH_2)_n$—OCONHR' wherein n is 4 to 12, R" and R' are the same or different, and wherein R" and R' are alkyl, alkali metal salts of acid alkyls, alkoxyalkyl, aryl, arylalkyl, haloalkyl, and haloaryl. Preferred diruethane diynes include the alkyl, alkoxyalkyl, and acid alkyl derivatives.

Suitable alkyl diurethane diynes are represented by the formula [AHNOCO$(CH_2)_n$—C≡C$]_2$ wherein A is an alkyl group of 1 to 18 carbons and n is an integer from 4 to 12. Representative alkyl diurethanes diynes are indicated by the above formula with A and n as represented in Table I.

TABLE I

| A | n |
|---|---|
| methyl (I) | 4 |
| ethyl (II) | 4 |
| n-propyl (III) | 4 |
| n-butyl (IV) | 4 |
| n-pentyl (V) | 5 |
| n-hexyl (VI) | 7 |
| n-heptyl (VII) | 9 |
| n-octyl (VIII) | 8 |
| n-nonyl (IX) | 9 |
| n-decyl (X) | 6 |
| n-undecyl (XI) | 6 |
| n-dodecyl (XII) | 5 |
| n-tridecyl (XIII) | 4 |
| n-tetradecyl (XIV) | 4 |
| n-pentadecyl (XV) | 8 |
| n-hexadecyl (XVI) | 9 |
| n-heptadecyl (XVII) | 12 |
| n-octadecyl (XVIII) | 7 |

The preferred alkyl diurethane monomers which are useful in the practice of this invention are the methyl, ethyl, and n-butyl derivatives where n=4 referenced in Table I as monomers I, II, and IV.

Suitable alkoxyalkyl diurethane diynes are represented by the formula [B—OOCCH$_2$NHOCO$(CH_2)_n$—C≡C$]_2$ wherein B is an alkyl group of 1 to 18 carbons and n is an integer from 4 to 12. Representative alkoxyalkyl diurethane diynes are indicated by the above formula with B and n as represented in Table II.

TABLE II

| B | n |
|---|---|
| methyl (I) | 4 |
| ethyl (II) | 4 |
| n-propyl (III) | 4 |
| n-butyl (IV) | 4 |
| n-pentyl (V) | 6 |
| n-hexyl (VI) | 5 |
| n-heptyl (VII) | 7 |
| n-octyl (VIII) | 5 |
| n-nonyl (IX) | 10 |
| n-decyl (X) | 8 |
| n-undecyl (XI) | 6 |
| n-dodecyl (XII) | 4 |
| n-tridecyl (XIII) | 4 |
| n-tetradecyl (XIV) | 4 |
| n-pentadecyl (XV) | 4 |
| n-hexadecyl (XVI) | 4 |
| n-heptadecyl (XVII) | 7 |

TABLE II-continued

| B | n |
|---|---|
| n-octadecyl (XVIII) | 9 |

The preferred alkoxyalkyl monomers which are useful in the practice of this invention are the methyl, ethyl and n-butyl derivatives where n=4 referenced in Table II as monomers I, II and IV.

The most preferred alkoxyalkyl urethane for the practice of this invention is 5,7-dodecadiyn-1,12-bis-butoxycarbonylmethyleneurethane (i.e. B is n-butyl and n is 4).

Suitable acid alkyl urethane diynes which may be utilized in the practice of this invention are represented be the formula [HOOCCH$_2$NHOCO$(CH_2)_n$—C≡C$]_2$ wherein n is 4–12. The preferred acid alkyl urethane diyne is 5,7-dodecadiyn-1,12-bis-carboxylmethylene urethane where n is 4 in the above formula. Additionally, it is preferred to convert 5,7-dodecadiyn-1,12-bis-carboxylmethylene urethane to its sodium, potassium, or lithium salt for the practice of this invention with the most preferred salt being the potassium salt.

Monomers suitable for constructing the defrost indicators of this invention can be prepared in general by known methods as described in U.S. Pat. No. 3,999,946, supra. For example, the bisurethane derivatives can be prepared by reacting the corresponding diyn-diol with a suitable isocyanate: Thus 5,7-dodecadiyn-1,12-bis-n-octadecylurethane has been prepared by reacting 5,7-dodecadiyn1,12-diol with n-octadecylisocyanate. A catalyst may be added to the reaction mixture to increase the reaction rate to produce the desired diacetylenic monomer. Conventional tin catalysts (e.g., dibutyltin-di-2-ethylhexanoate, DBTE), and tertiary amines (e.g., triethylamine, TEA) have been used as catalysts. The reaction mixture may also be warmed as, for example, to about 45° to 55° C., to speed up the reaction. Such heating, however, is not required. The desired diyndiol can also be prepared by conventional methods. Thus, for example, 5,7-dodecadiyn1,12-diol has been prepared by the oxidative coupling of the corresponding alkyne, i.e., 5-hexyn-1-ol. In similar fashion, the bisulfonate derivatives may be prepared by reacting the corresponding diyn-diol with a suitable sulfonyl chloride.

Monomers having more than four methylene groups in the main chain (n=5–12) are preferably synthesized using an alkynoic acid as a starting reagent. The alkynoic acid is converted to a sodium salt which may be oxidatively coupled by adding the acid-salt to a medium composed of N,N,N',N'-tetramethylethylene diamine, cuprous chloride and tetrahydrofuran while moderately bubbling oxygen into the medium. This coupling reaction should preferably be conducted at temperatures between about 60° C. and about 65° C. The coupled acid-salt is then converted to a diacid by general acidification procedures, and the diacid may then be reduced to the diyn-diol by employing lithium aluminum hydride as a reducing agent. The diyndiol is then reacted with a suitable isocyanate as described above to produce the desired monomer. Example 7 of this application includes 10,12-docosadiyn-1,22-bis-n-butoxycarbonylmethylene urethane (9BCMU) which was synthesized according to the described synthesis wherein 10-undecynoic acid was employed as the precursor material. Additionally, it should be noted that acid alkyl urethane diynes are preferably synthesized in accordance with the procedures described in copending commonly assigned application No. 159,741 now U.S. Pat. No. 4,373,032 issued 2-8-83.

Following preparation of the desired monomer, it is generally crystallized from an appropriate solvent, from the melt, or from the vapor so as to provide a solid monomer, preferably in a substantially crystalline phase, which is polymerizable. Suitable solvents employed in solution crystallization include alkyl esters of monocarboxylic acids, alkyl alcohols, paraffins, olefins, benzenes, alkylated benzenes, ethers, ketones, petroleum ether, halogenated hydrocarbons and water. Representative examples include ethyl acetate, methyl propionate, methanol, ethanol, butanol, isopropanol, hexane, heptane, 1,4-dimethylheptane, toluene, xylene, trimethylbenzene, ethylether, isopropylether, 1,2-dimethoxyethane, tetrahydrofuran, dioxane, acetone, ethylmethyl ketone, chloroform, dichloromethane and trichloromethane and mixtures thereof. Especially preferred as crystallizing solvents are isopropyl ether, 1,2-dimethoxyethane, dioxane, tetrahydrofuran, petroleum ether, acetone, chloroform, benzene, methanol, ethanol, xylene, ethyl acetate and water. Conventional crystallization procedures may be used such as by sublimation or by cooling a saturated solution to a sufficiently low temperature. Crystallization may, for example, be effected by room temperature evaporation of solutions containing from 0.0001 to 0.5 part, and preferably about 0.002 to 0.2 part by weight of monomer per part by weight of solvent or solvent blend.

Following recrystallization, the diacetylenic monomers are dissolved in solvents, frozen, and partially polymerized via irradiation in order to construct the activated defrost indicators. The solvent utilized for dissolving the monomer depends upon the nature of the monomer. In particular, polar solvents and moderately polar solvents which freeze in the $-20°$ C. to $20°$ C. range are preferably used for symmetrical monomers. Representative solvents for symmetrical monomers include acetic acid, propanoic acid, heptanoic acid, nonanoic acid, hydroxy acetone, 1,1,3,3-tetramethylurea, triethanolamine, n-decylamine, sec-phenethyl alcohol, ethyl ester of cinnamic acid, triacetal glycerol, diethyl sebacate, decyl ester of decanoic acid, monoethyl ester of succinic acid, dimethyl sulfoxide, p-xylene, and mixtures of ortho, meta, and para xylene. Additionally, water is a suitable solvent for alkali metal salt systems as described in Example 8 of this application. In a preferred embodiment of this invention acetic acid is the preferred solvent when symmetrical monomers are utilized.

Moderately polar and non-polar solvents which freeze in the $-20°$ C. to $20°$ C. range are more amenable to unsymmetrical diacetylenic monomers. Representative examples of moderately polar and non-polar solvents which are utilized in this invention include p-xylene, 4-chlorotoluene, 2-chloro-p-xylene, 3-methyl biphenyl, dodecane, tetradecane, 1-hexadecene, 1-heptadecene, 1-pentadecyne, 10-methyl stearic acid, ethyloctyl-ether, 3,3-dimethyl-2-butanol, cycloheptanol, 4-methylcyclohexanol, 10-undecen-1-ol, and triethylene glycol with p-xylene being the preferred solvent for non-polar diacetylenic monomers.

It is also possible to use combinations of the above solvents when constructing the defrost indicators of the present invention. By utilizing combinations of solvents in varying ratios, one can design defrost indicators which evidence a color transformation at a specific temperature. Example 9 of this application illustrates the combination of two solvents for the practice of the present invention.

It will be appreciated that the solvent must be compatible with the monomer. As the number of methylene groups of the monomer increases, whether said methylene groups are in the side or main chain, a less polar solvent must be employed. For example, where n equals 4 and A is ethyl in Table I or II above, acetic acid is a suitable solvent. However, where n equals 9 and A is octadecyl in Table I or II, a less polar solvent such as chlorobenzene should preferably be employed.

The monomer concentration in the solution may also be varied in order to construct defrost indicators which are appropriate for a particular product. The reason is that as the concentration of the monomer increases, the temperature at which the activated indicator completely changes color during defrost also increases. Naturally, this fact mandates that the time required for the indicator to change color will increase when the indicator is subjected to gradual increases of temperature. Therefore, depending upon whether one desires an indicator that changes colors at a higher or lower temperature, the concentration of the monomer in the solvent should be increased or decreased accordingly. For instance, a 5% solution of 5,7-dodecadiyn-1,12-bis-methylurethane in acetic acid exhibits a complete color transition at $14.2°$ C., whereas a 10% solution of 5,7-dodecadiyn-1,12-bis-methylurethane in acetic acid exhibits a complete color transition at $18.8°$ C.

The unactivated indicators may be fabricated by several methods. One method of fabricating the indicators involves employing a 0.95 cm square of filter paper as a substrate. The filter paper is surrounded by polychlorotrifluoroethylene, polyethylene, or other suitable plastic film, and the film is sealed on three sides with an impulse sealer. Polychlorotrifluoroethylene and polyethylene are each ultraviolet transparent. The indicator solution is then added through the open end. Preferably, the indicator solution should fill half of the packet. Fabrication of the unactivated indicators by this method is completed by sealing the remaining open end of the packet. Another method of fabricating the unactivated indicators is by microencapsulation of the indicator solutions, preferably using microencapsules which will not rupture during the freezing process. This embodiment eliminates the necessity for a protective film in the indicator device.

The described unactivated indicators can be conveniently shipped to users without regard to temperature exposure, since the unactivated (unpolymerized) monomer is stable in solution provided that the activation process is not employed. This is important as it would be inconvenient and expensive to utilize defrost indicators which had to be kept frozen from the time they were manufactured.

The unactivated defrost indicators are prepared for activation by freezing the indicators so that the encased solution of monomer and solvent solidifies. Freezing of the indicators may be accomplished by cooling the indicator solution to a temperature sufficient to cause solidification. For example, for devices which monitor frozen foods, the indicator can be placed in a freezer which operates between about $-20°$ C. and about $-25°$ C. Alternately, several defrost indicator solutions may be frozen at about $-78°$ C. by placing the indicators on a pulverized dry-ice bed for a short period of time.

Illustrative examples of indicator solutions which may be frozen at dry-ice temperatures include 5,7-dodecadiyn-bis-1,12-methylurethane, 5,7-dodecadiyn-bis-1,12-ethylurethane, and 5,7-dodecadiyn-bis-1,12-n-butylurethane. The described examples which may be frozen at dry-ice temperatures are important because certain perishable products require extremely low temperatures at all times prior to use. Therefore, it becomes important to have defrost indicators which can be activated during exposure to very low temperatures.

Freezing the encased indicator solutions results in the production of a novel article of manufacture. In particular, the article of manufacture comprises a phase of crystalline diacetylenic monomer 14 which is dispersed in a solid solvent phase 12 as represented in FIG. 2.

An additional method for producing the defrost indicators and this novel article of manufacture involves immersing a filter paper substrate in a solution comprised of diacetylenic monomer and solvent and then allowing the solvent to evaporate from the filter paper. The filter paper with deposited diacetylenic monomer is then sealed in a polychlorotrifluoroethylene, polyethylene or other similar plastic pouch which contains the microencapsulated solvent. The container with the filter paper substrate is then frozen and the microencapsules are ruptured via applied mechanical pressure or stress associated with the volume change on solidification, thereby resulting in frozen solvent admixed with the diacetylenic monomer as represented by FIG. 2.

Subsequent to the freezing of defrost indicator solutions, the indicator solutions are activated by subjecting the indicators to high energy radiation in order to activate the defrost indicators.

As previously indicated, suitable forms of radiation include ultraviolet light, electron beam, gamma rays, etc. Ultraviolet light is the preferred form of radiation for the practice of this invention. The radiation induces partial polymerization of the diacetylenic monomer, and is evidenced by the development of color in the previously colorless indicators (FIG. 3).

The amount of time required to activate the defrost indicator depends upon the power of the ultraviolet light source. If a high-powered ultraviolet lamp is used, one second of radiation will usually suffice to activate the indicators. On the other hand, if a low-powered ultraviolet lamp is utilized, it is necessary to irradiate the indicator for longer periods of time. In a preferred embodiment of this invention, the indicators are irradiated between about 15 and 30 seconds when a low-powered ultraviolet lamp is utilized. It is important to note that dependent on the particular diacetylene, the temperature at which the defrost indicator begins the color transition and the temperature at which the defrost indicator completes the color transition is dependent upon the total amount of radiation. The higher the amount of irradiation, the higher the beginning and completion color transition temperatures will be. Thus, one can also vary the radiation time in order to construct a defrost indicator for a particular product. Example 13 illustrates the use of varying amounts of irradiation in the construction of defrost indicators which function at different temperatures.

It will be appreciated that other methods of activation to produce the first article of manufacture of the invention are possible which are not included in the process of this invention. For example, activation may be accomplished via mechanical stress, thermal annealing in the solid state, or by an activating fluid, gas, or radical.

The partial polymerization of the phase of crystallized monomer 14 dispersed in the solid solvent phase 12 results in the production of an additional novel article of manufacture. The additional novel article of manufacture comprises a phase 16 of unpolymerized colorless monomer and colored polymer wherein the described phase is dispersed in the solid solvent phase 12.

It will be appreciated that there are also other methods of producing this article of manufacture. One such method initially involves depositing a diacetylenic monomer on a paper substrate and partially polymerizing the monomer so that a mixture of monomer and polymer results. Following partial polymerization of the monomer, the monomer-polymer mixture and paper substrate are frozen at a very low temperature between about $-50°$ C. to $-70°$ C. and then a solvent is sprayed onto the frozen monomer-polymer mixture and substrate. Upon contact with the frozen mixture and substrate, the solvent immediately solidifies thereby resulting in the solid solvent phase 12 which contains a phase 16 of unpolymerized colorless monomer and colored polymer as represented by FIG. 3.

Similarly, this article of manufacture may be produced by irradiating the frozen substrate having deposited monomer following the spraying of the solvent onto the frozen substrate. Production of the articles of manufacture represented by FIG. 3 by the procedures which involve spraying a solvent onto the substrate is illustrated by Examples 11 and 12.

The term partial polymerization is used to describe a process which results in an intimate mixture of monomer and polymer, containing, for example, between about 1 and 50 weight percent polymer, obtained by polymerizing the acetylenic compositions which are the subject of this invention. In the preferred embodiment of this invention, the mixture of monomer and polymer contains between about 2 and about 10 percent polymer.

An attractive advantage of the present invention is that the frozen indicator solutions require only 15 to 30 seconds of radiation under a low intensity ultraviolet light in order to effect activation at $-25°$ C. The dosage of the radiation required to activate the indicators is also a function of temperature. Higher temperatures will in general require shorter periods of exposure to ultraviolet radiation and conversely, lower temperatures will generally require longer periods of exposure to ultraviolet radiation in order to activate the indicators. A high intensity ultraviolet light source may be employed to decrease the time required for activation, since this time is roughly inversely related to exposure intensity. Activation, as previously discussed, is evidenced by the generally colorless indicators developing a brilliant color. Activation may occur prior to or subsequent to attachment of the indicator to the perishable.

The activated defrost indicator will retain its activated color as long as the perishable item is not exposed to temperatures which may possibly result in degradation of the perishable commodity. However, when the perishable commodity is exposed to temperatures which will cause degradation of the commodity, the solid solvent phase 12 melts and extracts the unpolymerized monomer from the polymer thereby inducing a color transition in the indicator (e.g. blue to red). The temperatures and the time required for the extraction to effect the complete color change is dependent upon the concentration of the monomer in the solvent, the particular monomer, the solvent or combination of solvents used and the degree of polymerization (i.e., time of exposure to radiation).

EXAMPLES

In examples 1 through 14 the following abbreviations are used: a) 4BCMU refers to 5,7-dodecadiyn1,12-bis-butoxycarbonylmethylene urethane, indicated as compound IV in Table II; b) MTCD refers to 5,7-dodecadiyn-1,12-bis-methylurethane, indicated as compound I in Table I; c) ETCD refers to 5,7-dodecadiyn-1,12-bis-ethylurethane, indicated as compound II in Table I; d) BTCD refers to 5,7-dodecadiyn-1,12-bis-n-butylurethane, indicated as compound IV in Table I; e) ECMU refers to 5,7-dodecadiyn-1,12-bis-ethoxycarbonylmethylene urethane, represented as compound II in Table II; f) 4HAU-Li refers to the lithium salt of 5,7-dodecadiyn1,12-bis-carboxylmethylene urethane; g) 4HAU-Na refers to the sodium salt of 5,7-dodecadiyn-1,12-bis-carboxylmethylene urethane; and h) 4HAU-K refers to the potassium salt of 5,7-dodecadiyn-1,12-bis-carboxylmethylene urethane; i) 4MCMU refers to 5,7-dodecadiyn-1,12-bis-methoxycarbonylmethylene urethane indicated as compound I in Table II; j) 4HCMU refers to 5,7-dodecadiyn-1,12-bis-n-hexoxycarbonylmethylene urethane; and k) 9BCMU refers to 10,12-docodiyn-1,22-bis-n-butoxycarbonylmethylene urethane.

EXAMPLE 1

4BCMU was synthesized as described in copending application No. 938,292 now U.S. Pat. No. 4,439,346, issued 3-27-84. A 10% (weight/volume) indicator solution of 4BCMU in acetic acid was prepared by dissolving 0.5 g 4BCMU in 5 mL of glacial acetic acid (m.p., 16.6° C.). A 0.95 cm square of Whatman's #1 filter paper was employed as a substrate for the indicator solution. The filter paper was sealed in polyethylene film (0.0762 mm) on 3 sides with an impulse-sealer. Polyethylene is UV transparent. The indicator solution was added through the open end so as to half fill the packet, and then the remaining open side was sealed. The packet containing the indicator solution and substrate (hereinafter referred to as indicator) was frozen at −25° C. Subsequent to freezing the indicator at −25° C., the indicator was irradiated with ultraviolet light using a UV lamp Model UVS-11E (Ultra Violet Products, Pasadena, Calif.).

Irradiation of the indicator caused the colorless indicator to develop a dark blue color. Upon thawing, the blue color changed to red and remained red even though the indicator was refrozen.

EXAMPLE 2

Example 1 was repeated except that the indicator was frozen for 5 minutes on a dry-ice bed (−56° C.). The indicator would not activate (develop blue color) when subjected to ultraviolet radiation. The temperature was increased to −25° C. and activation readily occurred. This indicated that activation for 4BCMU indicators should preferably be conducted at the higher temperature in order to avoid the necessity of employing high ultraviolet dosages.

EXAMPLE 3

A 10% solution (weight/volume) of ETCD/acetic acid was prepared and fabricated into indicators as described in Example 1. The ETCD indicators were frozen at −25° C. (freezer) or −78° C. (dry ice). The ETCD indicators which had been frozen were irradiated with ultraviolet light for 15 seconds. In each case activation readily occurred, evidenced by the development of a blue color in the previously colorless solid indicators. The indicators changed from a blue color to a vivid red color upon thawing.

EXAMPLE 4

A 5% solution (weight/volume) of 4BCMU/p-xylene (m.p., 13.3° C.) was prepared and fabricated into indicators as described in Example 1. The indicator packets were frozen in a freezer (−20° to −25° C.), placed on a dry-ice bed, and immediately irradiated with ultraviolet light for a period of 15 to 30 seconds. Irradiation of the indicators was accompanied by the development of a blue color in the indicators. The indicator exhibited a blue to red color transition upon thawing.

EXAMPLE 5

Solutions of ETCD in acetic acid (10% and 20% weight/volume) were prepared and fabricated into indicators as described in Example 1. The indicators were frozen at −25° C. in a freezer and then placed on a pulverized dry-ice bed. Next, the indicators were irradiated with UV light for periods of 30 and 120 seconds, respectively. Irradiation of the colorless indicators resulted in the colorless indicators changing to a blue color. Following irradiation, the blue colored indicators were immersed in a controlled temperature bath and the temperature was raised gradually until the color transition from blue to red occurred. The temperatures at which one-half the area of the indicator tabs appeared red, and the temperatures at which the entire tabs appeared red were recorded. The results appear in table III.

TABLE III

| Conc (%) | Initial Color | UV Exposure (Sec) | Color Following Irradiation | Temp (°C.), ½ Red | Temp (°C.), Completely Red |
|---|---|---|---|---|---|
| 10 | clear | 30 | dark blue | — | 9.0 |
| 10 | clear | 120 | dark blue | 8.5 | 9.8 |
| 20 | clear | 30 | dark blue | 9.0 | 10.8 |
| 20 | clear | 120 | dark blue | 9.8 | 11.0 |

The results indicate only a small difference in the temperature of the color transformations depending upon whether a 10% or a 20% solution was employed or whether the irradiation period was 30 seconds or 120 seconds. However, it should be noted that an increase in concentration results in a longer color transformation time.

EXAMPLE 6

Solutions of ETCD, 4BCMU, BTCD, and MTCD in acetic acid (10% weight/volume) were fabricated into indicators as described in Example 1. Additionally, a 5% solution in acetic acid was prepared for MTCD and ETCD, and a 10% solution in t-butanol was prepared for 4BCMU. The object of this particular experiment was to compare ETCD as a defrost indicator with MTCD, BTCD, and 4BCMU. The indicators were frozen at −25° C. in a freezer and then placed on a pulverized dry-ice bed and immediately irradiated for 15 seconds. All indicators turned dark blue upon being irradiated. Again, as in Example 5 the frozen and activated indicators were placed in a controlled temperature bath, and the temperature was raised gradually until the color transformation from blue to red occurred. The results are indicated in Table IV.

TABLE IV

| Ind. | Conc. (%) | Temp (°C.) ½ Red | Temp (°C.), Completely Red | Solvent |
|---|---|---|---|---|
| MTCD | 5 | 13.7 | 14.2 | Acetic Acid |
| MTCD | 10 | 11.7 | 18.8 | Acetic Acid |
| ETCD | 10 | 7.9 | 10.0 | Acetic Acid |
| 4BCMU | 10 | 17.9 | 19.6 | t-butanol |
| ETCD | 5 | 22.0 | 24.5 | t-butanol |
| BTCD | 10 | 8.4 | 9.4 | Acetic Acid |
| 4BCMU | 10 | — | 5.5 | Acetic Acid |

The lowest temperature was noted for 4BCMU in acetic acid (10%) and the highest temperature was noted for ETCD in t-butanol (5%); the former indicates 5.5° C., while the latter indicates 24.5° C. for total color transformation. A 4.6° C. difference is indicated between the results obtained for the 5 and the 10% concentration of MTCD in acetic acid.

EXAMPLE 7

Solutions of 4MCMU, 4HCMU, and 9BCMU in acetic acid (10% weight/volume) were prepared and fabricated into indicators as described in Example 1. The indicators were frozen at −25° C. in a freezer, placed in a dry-ice bed, and then irradiated with ultraviolet light for a period of 10 to 20 seconds. Irradiation of the indicators was accompanied by the development of a blue color in the indicators. The indicators exhibited a blue to red color transition upon thawing. The temperatures at which the color transitions occurred are listed in Table V. Also, the temperature at which 4BCMU exhibits a blue to red color transition is included in this table (data from Example 6).

TABLE V

| Ind | Temp (°C.), Color Transition |
|---|---|
| 4MCMU | −16.5° C. |
| 4BCMU | +5.5° C. |
| 4HCMU | +9.5° C. |
| 9BCMU | +70.0° C. |

The number of methylene groups increases in the order of 5, 8, 10, and 13 for 4MCMU, 4BCMU, 4HCMU, and 9BCMU, respectively. Therefore, the above results demonstrate that an increase in the number of methylene groups in the main and/or side chain decreases the overall polarity, thereby increasing the temperature for the complete color transition.

EXAMPLE 8

Solutions of LiOH, NaOH, and KOH (.2N) were prepared by adding 0.48 g LiOH, 0.8 g NaOH, and 1.1 g KOH, respectively, to 100 mL volumetric flasks and filling the flasks to the mark with distilled water. The indicator compositions 4HAU-Li, 4HAU-Na, and 4HAU-K were obtained by stoichiometrically mixing 2.5 mL of the respective stock solutions (LiOH, NaOH, and KOH) with 0.1 g 4HAU. The indicator devices were fabricated as described in Example 1 and then frozen between −20° C. to −25° C. The indicator devices were then irradiated with ultraviolet light as in the previous examples. The 4HAU-Li and 4HAU-K composition devices required 30 seconds to become completely blue; the 4HAU-Na composition device required 150 seconds (2½ min.) to become completely blue. The color of all three indicator devices changed from blue to orange-red upon thawing.

The samples were recycled twice by refreezing (the color of the samples on refreezing is the same red-orange as the thawed samples), irradiating each sample again with an ultraviolet lamp, and thawing the reirradiated samples. Reirradiation of the 4HAU-Li and 4HAUNa composition indicators resulted in the red-orange color changing to the blue color which accompanied the initial irradiation. However, the 4HAU-K composition indicator developed only a small amount of blue color. On the second recycling of the 4HAU-K indicator, the blue color failed to develop at all upon reirradiation.

EXAMPLE 9

A 4HAU-K indicator was prepared as in Example 8. The indicator was irradiated for 90 seconds. The irradiation of the indicator resulted in the colorless indicator changing to a dark blue color. The indicator was thawed, and the indicator changed to a red-orange color upon thawing. The indicator was refrozen as in Example 8 and irradiated for 90 seconds with ultraviolet light following refreezing. Reirradiation did not result in the development of any blue color in the indicator.

This experiment indicates that the 4HAU-K indicator can be rendered foolproof by utilizing an initial irradiation time of 90 seconds.

EXAMPLE 10

Four 2.5% (weight/volume) solutions of ETCD were fabricated into indicators as described in Example 1. Indicator number 1, hereinafter referred to as A, utilized acetic acid as a solvent. Indicator number 2, hereinafter referred to as 9A1P, utilized a solution comprised of 90% acetic acid and 10% propionic acid as a solvent. Indicator number 3, hereinafter referred to as 8A2P, utilized a solution comprised of 80% acetic acid and 20% propionic acid as a solvent. Indicator number 4, hereinafter referred to as P, utilized propionic acid as a solvent. The four unactivated defrost indicators were then frozen at −56° C. on a pulverized dry-ice bed and irradiated for 30 seconds with a UV lamp. Irradiation caused each of the indicators to develop a blue color. The defrost indicators were then immersed in a controlled temperature bath, and the temperature was then gradually raised until the color transition from blue to red occurred. The temperatures at which one-half the area of the indicator tabs appeared red and the temperatures at which the entire tabs appeared red were recorded. The results appear in Table VI.

TABLE VI

| Indicator | Temp. (°C.), ½ Red | Temp. (°C.), Completely Red |
|---|---|---|
| A | 9.3 | 14.8 |
| 9A1P | 4.8 | 7.1 |
| 8A2P | −4.6 | 7.3 |
| P | — | −20.9 |

The above results indicate that propionic acid significantly depresses the temperature at which defrost indicators using acetic acid as a solvent undergo the blue to red transition. Also, the above results indicate that propionic acid is an excellent solvent for defrost indicators for products which must not be exposed to temperatures above −21° C.

EXAMPLE 11

A small square of Whatman's filter paper was immersed in a 10% solution of ETCD in acetic acid. The solvent (acetic acid) was allowed to evaporate from the filter paper, and then the filter paper was frozen at −60° C. and irradiated for 30 seconds with an ultraviolet lamp. The filter paper turned blue upon irradiation. The blue colored filter paper, frozen at −60° C., was then sprayed with acetic acid using a Crown SPRA-A-TOOL (No. 8011 Power Pak). The acetic acid froze immediately upon contact with the substrate (filter paper with partially polymerized monomer). The frozen and blue colored filter paper was then allowed to thaw gradually at room temperature. Upon thawing, the filter paper exhibited a blue to red color transition.

EXAMPLE 12

The procedure of Example 11 was repeated except that irradiation followed the spraying of acetic acid instead of occurring prior to the spraying of the acetic acid. A blue to red color transition occurred upon thawing of the device.

EXAMPLE 13

A defrost indicator was constructed by initially immersing a small square of filter paper in a 10% (weight/volume) solution of 4BCMU in acetone. The acetone was allowed to evaporate from the filter paper, the filter paper was irradiated (resulting in a blue colored filter paper) and then the blue colored filter paper was sealed in a 0.127 mm polychlorotrifluoroethylene pouch which contained microencapsuled xylene (Xylene Lot #CJTW-353, NCR, Appleton Papers Division, Dayton, Ohio). The polychlorotrifluoroethylene container was frozen over a dry-ice bed at −78° C., crushed with a spatula, and quickly placed in a temperature bath at −21° C. The temperature of the bath was gradually raised and the temperature at which color transitions were observable were recorded. The indicators were 50% red and 50% blue at −4° C., and the complete blue to red color transition occurred at 1° C.

EXAMPLE 14

A solution of ETCD in acetic acid (10% weight/volume) was prepared and fabricated into a defrost indicator as described in Example 1, except that the size of the indicator was 11.2×5.1 cm. The indicator was frozen at −25° C. The indicator was covered with Mylar ® plastic film (which blocks out UV) except for a strip corresponding to about one sixth of the indicator and was then irradiated for 1 second with a high-powered short wavelength ultraviolet light source (Xenon Corp. Model #RC250). The Mylar ® was then positioned so that one third of the indicator was exposed (the one-sixth strip already irradiated and an additional one-sixth strip which had been protected from the initial irradiation). The exposed section of the indicator was irradiated for one second with the high-powered UV lamp. This procedure was repeated three times with the high-powered ultraviolet light source and three times with a low-powered ultraviolet light source until six strips with decreasing exposure to irradiation were obtained. The indicator was then placed in a controlled temperature bath and the temperature was gradually raised until a blue to red color transition occurred for each strip. The temperatures at which the strips began to exhibit a blue to red transition, and the temperatures at which the color transition were complete were recorded. The results appear in Table VII.

| Indicator Strip | UV Exposure (Sec.) | Temperature °C. | | | | | | |
|---|---|---|---|---|---|---|---|---|
| | | 9.0 | 10.0 | 11.2 | 12.0 | 13.9 | 15.0 | 16.0 |
| 1 | 3H + 360S | | | | | | B | C |
| 2 | 2H + 360S | | | | | B | | C |
| 3 | 1H + 360S | | | B | | C | | |
| 4 | 360S | | B | | C | | | |
| 5 | 300S | | B | | C | | | |
| 6 | 240S | B | | | C | | | |

B = color transition beginning temperature
C = color transition completion temperature
H = high-powered ultraviolet lamp (Xenon Corp. Model #RC250)
S = short-powered ultraviolet lamp (Ultra Violet Products Model #UVS-11E)

The above results indicate that the strips which were irradiated for a longer period of time required a higher temperature in order to undergo the beginning and completion of the color transition from blue to red.

It should be pointed out that indicators 1–3 were irradiated with high powered and low powered ultraviolet light, whereas indicators 4–6 were irradiated with only a low-powered ultraviolet light source. For example, indicator No. 2 was irradiated for 2 seconds with high-powered ultraviolet light and 360 seconds with low-powered ultraviolet light. On the other hand, indicator No. 4 was irradiated for 360 seconds with a low-powered ultraviolet light source.

What is claimed is:

1. A process which comprises the steps:
   (a) dissolving a diacetylenic monomer in a solvent to form a solution of monomer and solvent;
   (b) freezing said solution to crystallize the diacetylenic monomer to form an intimate mixture of a phase of crystallized monomer and a solid solvent phase;
   (c) irradiating said phase of crystallized monomer to partially polymerize said crystallized monomer to form a phase of unpolymerized monomer and colored polydiacetylene;
   wherein said monomer is soluble in said solvent above the freezing point of said solvent.

2. The process of claim 1 wherein said solid solvent phase has a melting point within the range of −20° C. to 20° C.

3. The process of claim 1 wherein said solvent is acetic acid.

4. The process of claim 1 wherein the radiation is ultraviolet light, electron beam or gamma rays.

5. The process of claim 4 wherein said radiation is ultraviolet light.

6. The process of claim 1 wherein said monomer is a diurethane diyne.

7. The process of claim 6 wherein said diurethane diyne is of the following formula:

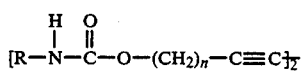

wherein n is 4–12 and R is an alkyl or an alkoxyalkyl group containing 1–18 carbons or is GOOCCH$_2$—, with G being alkyl of 1–4 carbons.

8. The process of claim 7 wherein R is GOOCH$_2$ and n is 4.

9. The process of claim 7 wherein R is an alkyl group containing 1-4 carbons and n is 4.

10. The process of claim 6 wherein said diurethane diyne is of the following formula:

$$[\text{MO-C(O)}-\text{CH}_2\text{NH}-\text{C(O)}-\text{O(CH}_2)_n-\text{C}\equiv\text{C}]_2$$

wherein n is 4–12 and M is potassium, sodium or lithium.

11. A process according to claim 10 wherein M is potassium.

* * * * *